(12) United States Patent
Rey et al.

(10) Patent No.: US 10,442,760 B2
(45) Date of Patent: Oct. 15, 2019

(54) CATALYTIC OXIDATION OF BUT-3-ENE-1,2-DIOL

(71) Applicant: ADISSEO FRANCE S.A.S., Antony (FR)

(72) Inventors: Patrick Rey, Lyons (FR); Virginie Belliere-Baca, Vourles (FR); Franck Dumeignil, Fretin (FR); Fabien Grasset, Grasse (FR)

(73) Assignee: ADISSEO FRANCE S.A.S., Antony (FR)

( * ) Notice: Subject to any disclaimer, the term of this patent is extended or adjusted under 35 U.S.C. 154(b) by 0 days.

(21) Appl. No.: 15/533,202

(22) PCT Filed: Dec. 7, 2015

(86) PCT No.: PCT/FR2015/053348
§ 371 (c)(1),
(2) Date: Jun. 5, 2017

(87) PCT Pub. No.: WO2016/087807
PCT Pub. Date: Jun. 9, 2016

(65) Prior Publication Data
US 2017/0342029 A1    Nov. 30, 2017

(30) Foreign Application Priority Data
Dec. 5, 2014   (FR) .................................... 14 61964

(51) Int. Cl.
| | | |
|---|---|---|
| *C07C 319/18* | (2006.01) | |
| *B01J 23/00* | (2006.01) | |
| *C07C 49/258* | (2006.01) | |
| *C07C 49/24* | (2006.01) | |
| *C07C 45/39* | (2006.01) | |
| *B01J 23/44* | (2006.01) | |
| *B01J 27/185* | (2006.01) | |
| *B01J 37/02* | (2006.01) | |
| *B01J 37/08* | (2006.01) | |
| *C07C 323/54* | (2006.01) | |
| *C07C 51/23* | (2006.01) | |
| *C07C 45/37* | (2006.01) | |
| *C07C 59/76* | (2006.01) | |
| *B01J 38/02* | (2006.01) | |
| *B01J 23/96* | (2006.01) | |
| *B01J 37/16* | (2006.01) | |
| *B01J 38/48* | (2006.01) | |
| *B01J 27/28* | (2006.01) | |

(52) U.S. Cl.
CPC .......... *C07C 319/18* (2013.01); *B01J 23/007* (2013.01); *B01J 23/44* (2013.01); *B01J 27/1856* (2013.01); *B01J 37/0201* (2013.01); *B01J 37/088* (2013.01); *C07C 45/37* (2013.01); *C07C 45/39* (2013.01); *C07C 51/23* (2013.01); *B01J 23/96* (2013.01); *B01J 27/285* (2013.01); *B01J 37/16* (2013.01); *B01J 38/02* (2013.01); *B01J 38/48* (2013.01); *B01J 2523/00* (2013.01); *Y02P 20/584* (2015.11)

(58) Field of Classification Search
None
See application file for complete search history.

(56) References Cited

U.S. PATENT DOCUMENTS

| | | | |
|---|---|---|---|
| 5,155,263 A | 10/1992 | Imanari et al. | |
| 7,662,997 B2 * | 2/2010 | Rey ....................... | C07C 51/245 562/538 |
| 2004/0204597 A1 * | 10/2004 | Mizuno ................. | B01J 23/462 554/115 |
| 2010/0113807 A1 * | 5/2010 | Ichihara ................ | B01J 23/007 549/512 |

(Continued)

FOREIGN PATENT DOCUMENTS

| | | |
|---|---|---|
| FR | 2880345 A1 | 7/2006 |
| JP | 62142134 A | 6/1987 |
| WO | 2013018626 A1 | 2/2013 |

OTHER PUBLICATIONS

Ebitani et al. ("Heterotrimetallic RuMnMn Species on a Hydrotalcite Surface as Highly Efficient Heterogeneous Catalysts for Liquid-Phase Oxidation of Alcohols with Molecular Oxygen", Angew. Chem., Int. Ed., vol. 44, pp. 3423-3426, 2005).*

(Continued)

*Primary Examiner* — Rosalynd A Keys
(74) *Attorney, Agent, or Firm* — Cantor Colburn LLP

(57) ABSTRACT

The invention concerns a synthesis process of a compound of the following formula (I) or one of the salts thereof,

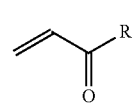

Formula (I)

wherein R represents a COOH, $CH_2OH$ or CHO group, comprising the step according to which the but-3-ene-1,2-diol (BDO) is subjected to an oxidation in the presence of a catalyst, said catalyst comprising an active phase based on at least one noble metal selected from palladium, gold, silver, platinum, rhodium, osmium, ruthenium and iridium, and a support containing alkaline sites.

The invention also concerns the application of this reaction to the preparation of bioavailable compounds of methionine used, in particular, in animal nutrition.

17 Claims, 1 Drawing Sheet

(56) References Cited

U.S. PATENT DOCUMENTS

2013/0137896 A1* 5/2013 Tani ...................... B01J 23/462
562/577

OTHER PUBLICATIONS

Mori et al. ("Hydroxyapatite-Supported Palladium Nanoclusters: A Highly Active Heterogeneous Catalyst for Selective Oxidation of Alcohols by Use of Molecular Oxygen", J. Am. Chem. Soc., Aug. 2004, vol. 126, No. 34, pp. 10657-10666.*
International Search Report dated Feb. 19, 2016 re: Application No. PCT/FR2015/053348; pp. 1-2; citing: FR 2 880 345 A1, JP S62 142134 A, WO 2013/018626 A1 and U.S. Pat. No. 5,155,263 A.

* cited by examiner

CATALYTIC OXIDATION OF BUT-3-ENE-1,2-DIOL

The present invention concerns the catalytic oxidation of but-3-ene-1,2-diol (BDO) and the application of this reaction for the preparation of bioavailable compounds of methionine and which, according to the invention, may be used in animal nutrition.

These compounds are 2-oxo-4-methylthiobutanoic acid (hereinafter called KMB), 4-methylthio-2-oxo-butanol (hereinafter called methionol), 2-oxo-4-methylthiobutanal (hereinafter called methional) and correspond to the structures hereinafter,

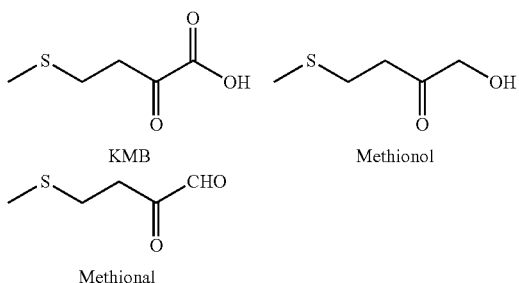

as well as the salts and esters thereof.

Figure 1:
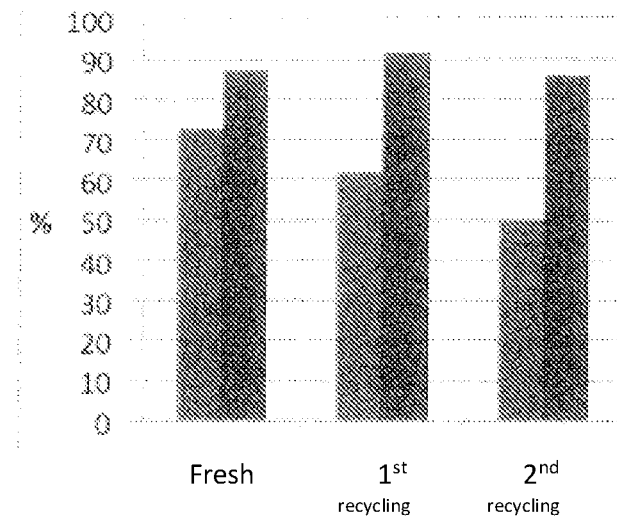
FIG. 1 shows BDO conversion and selectivity for hydroxybut-3-en-2-one (CALV) of Example 3 with catalyst 4.

The authors have developed a process for the preparation of the above compounds, in two steps and under conditions allowing limiting the reaction times while obtaining a good conversion efficiency of BDO and to further improve the selectivity of the reaction.

The first step involves the oxidation of BDO to the vinyl keto acid, 2-oxo-but-3-enoic acid (CAV), to the vinyl keto alcohol, hydroxybut-3-en-2-one (CALV), and to the vinyl keto aldehyde, 2-oxo-but-3-en-1-al (CADV), according to the following equations:

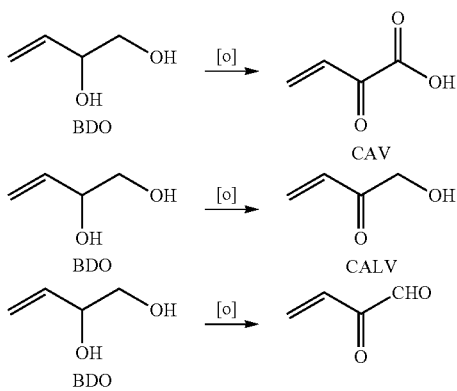

The second step consists in the addition of methyl mercaptan to the aforementioned keto-acid, -alcohol and -aldehyde according to the following equations:

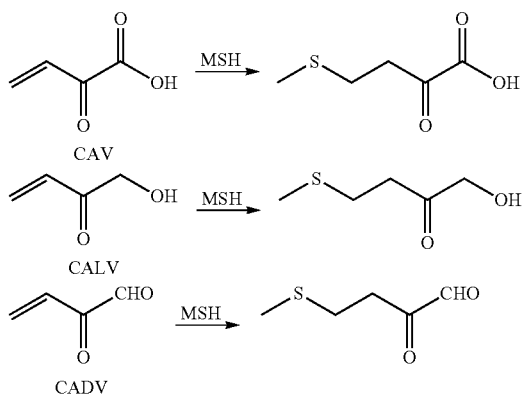

According to a first aspect of the invention, it concerns the oxidation of BDO carried out in the presence of a catalyst, said catalyst comprising an active phase based on at least one noble metal selected from palladium, gold, silver, platinum, rhodium, osmium, ruthenium and iridium, and a support containing alkaline sites. According to a variant of the invention, the active phase is based on palladium. When the active phase is based on palladium, it may consist of palladium; it may also consist of palladium and one or other noble metal(s).

In addition to the conversion efficiencies of BDO and the selectivity the oxidation thereof, the process of the invention allows eliminating any adjustment of the pH of the reaction medium and thus avoiding adding a base to the reaction medium. Relative the known processes implemented in the presence of sodium hydroxide, which results in the formation of salts requiring being neutralized and generating unwanted saline aqueous effluents, the process of the invention generates no salt and therefore there is no recourse to a subsequent processing step.

Before exposing the invention in further details, certain terms used in the text are defined hereinafter.

The term support containing alkaline sites means according to the invention a support containing surface sites presenting an electronic surplus; by way of example, these sites are constituted or rich in ions such as hydroxyl ion, $O^{2-}$ ion; preferably it is selected from hydrotalcite (HT) and hydroxyapatite (HAP). It may also be selected from conventional or alkaline supports, after they are modified in order to make them alkaline or more alkaline. These modifications consist in particular in replacing certain ions of the support, in attaching alkaline groups on the support or any other modification known to those skilled in the art. By way of example, HP may be modified to compounds called <<hydrotalcite-like>> (HTlc) as follows: HP corresponds to the exact formula $Mg_6Al_2(CO_3)(OH)_{16} \cdot 4H_2O$, and consists of cationic brucite $[Mg(OH)_2]$ layers between which there are anionic compounds to lead to a neutral material. It is possible to perform isomorphic substitutions within brucite layers in order to replace the $Mg^{2+}$ and $Al^{3+}$ ions. The ion exchange in the cationic layer and/or the anionic layer, inducing in particular a change in the Mg/Al ratio, allows adjusting the basicity of the support. As a result, the <<hydrotalcite-like>> (HTlc) compounds have the general formula $[M(II)_{1-x}M'(III)_x(OH)_2]^{x+} (A^{n-}_{x/n}) \cdot mH_2O$, wherein A is an anion, and M/M' are metal cations.

The alkaline character of a support according to the invention is characterized by its ability to give electron pairs or to accept protons. This notion of alkaline support belongs to the general knowledge of those skilled in the art. It may even have recourse to conventional techniques widely described in the literature. It may be noted, in particular, the techniques for characterizing the surface alkaline sites by infrared vibrational spectroscopy after adsorption of acid probe molecules (acetylene, methanol, $CO_2$, propyne, . . . ), by thermal desorption of $CO_2$, by $CO_2$ calorimetry, by model reaction (conversion of 2-methyl-3-butyn-2-ol (MBOH), . . . ).

A support of the invention may be in any shape, in particular any geometrical shape on which the active phase of the catalyst may be deposited. It may be porous.

The salts of the compounds obtained according to any one of the processes of the invention are preferably copper, calcium, manganese and zinc salts.

Other aspects of the invention, as well as preferred variants are exposed hereinafter. Of course, within the scope of the invention, the presented features may be considered alone or in combination.

As indicated beforehand, the active phase consists of a noble metal or a mixture of noble metals. Preferably, the noble metal is palladium, it may be also in a mixture with another noble metal, advantageously selected from platinum and gold.

The active phase content of a catalyst according to the invention advantageously ranges from 0.005 to 50% by weight of the one or more metal(s) constituting the active phase relative to the weight of the support in its oxide form.

The support is selected from hydrotalcites (HT), brucites, hydroxyapatite $Ca_{10}(PO_4)_6(OH)_2$, tricalcium phosphate $Ca_3(PO_4)_2$, calcium hydrogenphosphate $CaHPO_4(0-2)H_2O$, calcium diphosphate $Ca_2P_2O_7$, octacalcium phosphate $Ca_8H_2(PO_4)_6 \cdot 5H_2O$, tetracalcium phosphate $Ca_4(PO_4)_2O$, amorphous calcium phosphates $Ca_3(PO_4)_2 \cdot nH_2O$, oxides, hydroxides, carbonates, bicarbonates, phosphates, diphosphates, and calcium hydrogenphosphates, cesium, lithium, rubidium, strontium, potassium, magnesium, barium, cerium, lanthanum, aluminum, zinc and/or copper, and from all mixtures thereof.

Advantageously, the support is selected from the compounds corresponding to the following formulas A, B and C, and mixtures thereof:

$$M_\alpha[Al_{(1-b)}La_b]A^{z-}9_c \qquad \text{Formula (A)}$$

wherein

M is selected from the group composed of $Mg^{2+}$, $Ca^{2+}$, $Sr^{2+}$, $Ba^{2+}$, $Ra^{2+}$, and combinations thereof, $A^{z-}$ is a monovalent or divalent anion selected from the group composed of carbonate ($CO_3^{2-}$, wherein the charge «z» is given by z=2), oxide ($O^{2-}$, wherein z=2), hydroxide ($OH^-$, wherein z=1), and bicarbonate ($HCO_3^-$, wherein z=1) or a mixture ($A^{z'-}_x A^{z''-}_y$) of divalent and monovalent anions with $A^{z'-}$ and $A^{z''-}$ of different anions, with $A^{z-}$ is $A^{z'-}_x A^{z''-}_y$, with a charge z given by z=x(z')+y(z'') and x+y=1

α varies from 0.01 to 0.4 b varies from 0.0011 to 0.11

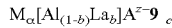

$$(M_dM'_eM''_fM'''_g)_5(PO_4)_3(OH) \qquad \text{Formula (B)}$$

wherein

M is $Mg^{2+}$, M' is $Ca^{2+}$, M" is $Sr^{2+}$, M''' is $Ba^{2+}$ d varies from 0 to 1 e varies from 0 to 0.5 f varies from 0 to 1 g varies from 0 to 1

$d+e+f+g=1$ $$(M_dM'_eM''_fM'''_g)_3(PO_4)_2 \qquad \text{Formula (C)}$$

wherein

M is $Mg^{2+}$, M' is $Ca^{2+}$, M" is $Sr^{2+}$, M''' is $Ba^{2+}$ d varies from 0 to 1 e varies from 0 to 1 f varies from 0 to 1 g varies from 0 to 1

$d+e+f+g=1.$

According to an embodiment of the invention, the catalyst comprises, besides the active phase and the support, a promoter. Said promoter is preferably selected from bismuth, lead, antimony, tin, niobium, tellurium, indium, gallium, zinc, copper, nickel, cobalt, silver, tungsten, molybdenum, zirconium, vanadium, chromium, manganese, iron, cerium, praseodymium, samarium, titanium and mixtures thereof.

According to other aspects of the invention, the catalytic conditions of the oxidation of BDO allow predominantly obtaining one of the aforementioned keto-acid, -alcohol and -aldehyde, or even obtaining only one of these three.

Thus, in an embodiment of the invention, the compound (I) is the vinyl keto-acid (CAV).

In another embodiment of the invention, the oxidation is carried out in the presence of a catalyst whose active phase is selected from palladium and the mixtures of palladium and platinum and the alkaline site support is selected from hydroxyapatite and hydrotalcites, and the compound (I) is the vinyl keto-alcohol (CALV).

In yet another embodiment of the invention, the compound (I) is the vinyl keto-aldehyde (CADV).

The invention also concerns the applications of a synthesis process as defined above.

Thus, it concerns the synthesis of at least one compound of the following formula (II) or one of the salts thereof,

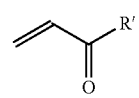

Formula (II)

wherein R' represents a group COOR1 or CH$_2$OR2 for which R1 and R2, identical or different, represent a group selected from the alkyl groups, linear or branched, having from 1 to 12 carbon atoms, and the cycloalkyl groups having from 3 to 12 carbon atoms, a synthesis in which:

the but-3-ene-1,2-diol (BDO) is subjected to an oxidation in the presence of a catalyst, said catalyst comprising an active phase based on at least one noble metal selected from palladium, gold, silver, platinum, rhodium, osmium, ruthenium and iridium, and a support containing alkaline sites, in order to obtain a compound of the following formula (I)

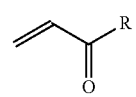

Formula (I)

wherein R represents a COOH, CH$_2$OH or CHO group, in any one of the conditions defined above, and the esterification or etherification of the compound of formula (I) is carried out in order to obtain the compound of formula (II).

Therefore, this synthesis gives access to the ester and alkoxylated derivatives of the compounds of Formula (I), which are also precursors of bioavailable compounds of the methionine of interest.

The invention also concerns a process for the synthesis of at least one compound of the following formula (III) or one of the salts thereof,

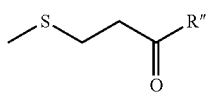

Formula (III)

wherein R" represents a COOH, COOR1, $CH_2OH$, $CH_2OR2$ or CHO group for which R1 and R2, identical or different, represent a alkyl group, linear or branched, having 1 to 12 carbon atoms, and the cycloalkyl groups having 3 to 12 carbon atoms, a synthesis in which:

but-3-ene-1,2-diol (BDO) is subjected to oxidation in the presence of a catalyst in order to obtain at least one compound of the following formula (I) or one of the salts thereof,

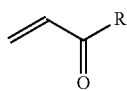

Formula (I)

wherein R represents a COOH, $CH_2OH$ or CHO group, according to the process described beforehand, if R" represents a COOR1 or $CH_2OR2$ group, an esterification or an etherification of the compound of formula (I) is carried out in order to obtain at least one compound of the following formula (II) or one of the salts thereof,

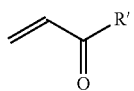

Formula (II)

wherein R' represents a COOR1 or $CH_2OR2$ group for which R1 and R2, identical or different, represent a group selected from the alkyl groups, linear or branched, having from 1 to 12 carbon atoms, and the cycloalkyl groups having from 3 to 12 carbon atoms, And, said compound (I) or said compound (II) or said one of the salts thereof is reacted with methyl mercaptan in order to obtain said compound (III) or one of the salts thereof, at least.

The adding of methyl mercaptan is performed under conditions well known to those skilled in the art. It may be carried out in the absence or in the presence of a solvent and a homogeneous base catalyst.

According to a variant of the process, the oxidation is carried out under the conditions allowing obtaining CAV, and the compound (III) is 2-oxo-4-methylthiobutyric acid.

According to another variant of the process, the oxidation is carried out under the conditions allowing obtaining the CALV and the compound (III) is 1-hydroxy-4-methylthiobutan-2-one.

According to yet another variant of the process, the oxidation is carried out under the conditions allowing obtaining CADV and the compound (III) is 2-oxo-4-methylthiobutanal.

The oxidation of BDO according to the invention is described hereinafter in further details.

The BDO may be in its liquid form, in the purified or unpurified state, or else in the form of a raw aqueous solution, that is to say of less purity, for example resulting from its preparation. According to a variant of the invention, the BDO is in aqueous solution in a concentration ranging from 1 to 70% by weight relative to the weight of the solution.

The BDO may be obtained from butadiene by monoepoxidation of said butadiene to 3,4-epoxy-1-butene which is converted to BDO (II) by chemical opening of the epoxide function, advantageously acid-catalyzed and in an aqueous medium.

Regardless of its form, the diol is directly usable for the catalytic oxidation reaction to 2-oxo-but-3-enoic acid (CAV), to hydroxybut-3-en-2-one (CALV) or to 2-oxobut-3-en-1-al (CADV). Advantageously, the aqueous solution which results from the opening of the above epoxide will be directly engaged in the oxidation step of BDO.

The noble metal-based BDO oxidation catalyst may comprise at least one promoter selected from bismuth, lead, antimony, tin, niobium, tellurium, indium, gallium, zinc, copper, nickel, cobalt, gold, silver, tungsten, molybdenum, rhenium, vanadium, chromium, manganese, iron, and mixtures thereof.

The promoter content is comprised between 0.005 and 500%, preferably between 0.005 and 100%, by weight relative to the weight of the support in the oxide form thereof. The deposition of the promoter on the catalytic support is advantageously carried out by impregnation.

The catalyst preparation is carried out by impregnation by maintaining under stirring the catalyst support and the solution containing the one or more noble metal(s) mixture, for a period varying from at least a few seconds to a few hours, generally comprised between 2 and 16 hours. The catalyst is then dried then optionally impregnated with the solution of the promoter. This operation precedes an optional calcinination step of the catalyst which is performed under static air at a temperature comprised between 20 and 800° C. A reduction of the catalyst may be performed at a temperature comprised between 20 and 400° C., using chemical reducing agent of the type formol, sodium formate, sodium borohydride, hydrogen, hypophosphorous acid, hydrazine, glucose or other reducing sugars.

An alternative preparation of the catalyst is to carry out a first impregnation of the promoter followed by a second impregnation step of the one or more noble metal(s). A reduction of the catalyst is then operated.

Another preparation alternative of the catalyst is to produce, in a single impregnation of the one or more noble metal(s) and the promoter. A reduction of the catalyst is then operated.

The reaction conditions of an oxidation of BDO according to the invention are described hereinafter in further details and are illustrated in the following examples:

an aqueous solution of BDO is introduced into a reactor provided with a stirring device, the BDO concentration being preferably comprised between 1 and 70% by weight. The lower limit of the diol concentration is dictated by a concern of cost effectiveness of the process and its higher limit takes into account the solubility of the oxygen in the considered media and the risk of crystallisation of the derivative formed during the reaction;

an amount of a catalyst, preferably supported and activated as described above is dispersed in this solution;

the oxidation reaction is initiated by the simultaneous provision of a sweeping of an oxygen-containing gas such as air.

The reaction temperature generally ranges from 10° C. to 95° C., preferably from 20° C. to 95° C., or even from 25° C. to 70° C., for a reaction time comprised between 20 minutes and 15 hours.

The process according to the invention allows reaching very interesting selectivities exceeding 90%. These performances are not distorted by an important number of recycling and/or reactivation of the oxidation catalyst implemented in accordance with the present invention. The used catalysts have a significant lifetime and are easily regenerated in situ by deposition of a new promoter charge or by reduction in situ of the deactivated catalyst.

This first oxidation step is, advantageously, practiced in an aqueous solvent. An organic solvent or a mixture of organic solvents may also be used. A hydro-organic medium may also prove to be advantageous.

The organic solvent, constituting the medium in which the oxidation reaction of BDO is performed, is selected from any solvent, at least partial, of said diol (BDO), inert under the operating conditions, in particular the one or more solvent(s) is/are advantageously selected from aliphatic, cycloaliphatic or aromatic hydrocarbons and in particular from:
- alkyl or alkenyl esters of aliphatic carboxylic acids; aliphatic, aromatic or cyclic ethers; aliphatic, cycloaliphatic or aromatic nitriles; aliphatic, cycloaliphatic or aromatic ketones. By way of non-limiting examples, there may be mentioned:
- hydrocarbons such as n-hexane, n-heptane, n-octane, n-nonane, benzene, styrene, ethylbenzene, toluene, metaxylene, isopropylbenzene, cyclohexane, methyl-4-pentene-2;
- esters such as ethyl formate, butyl formate, isobutyl formate, ethyl acetate, allyl acetate, propyl acetate, butyl acetate, hexyl acetate, ethyl propionate, vinyl propionate, ethyl acrylate, butyl butyrate, methyl isobutyrate; methyl butyrate;
- ethers such as cis-ethoxy-1-butene-1, trans-ethoxy-1-butene-1, dibutyl oxide, isopropoxy-1-butane, dimethoxy-1,1-ethane, diethoxy-1,1-ethane, dimethoxy-1,1-propane, ethoxy-1-butane, diisopropyl oxyde, ethoxy-1-hexane, ethoxy-2-propane, methoxy-1-butadiene 1,3, vinyl and butyl ether, furan, dimethyl-2,5-furan,
- nitriles such as butyronitrile, acetonitrile, acrylonitrile, propionitrile, tetrahydro benzonitrile;
- ketones such as cyclopentanone, dipropylketone, heptanone, methylisopropylketone, methyl-5-hexanone-2, pentanone-2, methyl-4-pentene-3-one.

The oxygen used to initiate the oxidation reaction may be molecular oxygen, air, oxygen-enriched or oxygen-depleted air, or any other mixture of oxygen with an inert gas.

The total pressure under which the reaction is performed may be greater than, equal to or lower than atmospheric pressure; it is generally comprised between 0.5 and 10 bars. The oxygen partial pressure is preferably, comprised between 0.05 bar and 5 bar. The oxidation of BDO may be performed either by maintaining a constant pressure, or by circulating oxygen or the gas containing it, in the apparatus where the reaction is performed, or else by bubbling oxygen or the gas containing it, into the reaction mixture.

The equipment in which the process according to the invention is implemented may not, of course, be specific to said process.

The condensation step of a compound (I) of the invention with methyl mercaptan in order to obtain a compound (II) in accordance with the invention is exposed hereinafter in details.

According to this step, one mole of methyl mercaptan (MeSH) in its gaseous or liquid form and one mole of CAV or of CALV or of CADV prepared beforehand are condensed according to the following reaction scheme:

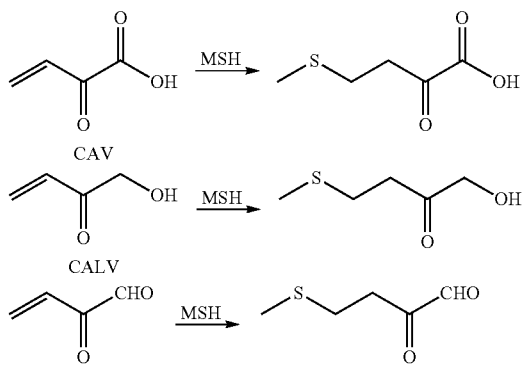

The field of the present invention is that of the manufacture of KMB, methionol, methional and mixtures thereof as a final product, or intermediate product. The reactivity of thiols is, in many aspects, similar to the reactivity of alcohols. They may, according to the implemented catalytic conditions, be added to α,β-unsaturated aldehydes, α,β-unsaturated ketones and α,β-unsaturated acids, in the 1,2 position leading to mono-hemithioacetal or in the 1,4 position leading to 3-alkylthiopropionaldehyde. By structural analogy, the vinyl ketoacids completely fall within the category of activated olefins.

Two catalytic ways are conventionally recommended in order to selectively and efficiently add the thiols in the position 4 on the α,β-unsaturated carbonyl derivatives. The first is a base-catalyzed ionic addition. The second is a radical addition initiated by the azo or peroxide compounds. However, this mode of initiation generally leads to most often undesirable polymers.

The Michael type 1,4 addition of the thiols on the α,β-unsaturated ketones is preferably used.

The starting raw product comprising KMB, methionol, methional, salified or not, may undergo a first processing allowing eliminating co-produced impurities during the oxidation of BDO. This raw product may also be subjected to a degassing. The excess BDO corresponding to the unreacted diol may advantageously be recycled in the oxidation step, for example, by distillation or extraction. The aqueous solution of CAV, CALV or CADV may, possibly, undergo a concentration prior to contacting with gaseous or liquid methyl mercaptan. It is then contacted with gaseous or liquid methyl mercaptan to lead to KMB, or methionol or methional.

This step may possibly, be performed in the presence of a catalyst or a mixture of alkaline catalysts. Suitable alkaline catalysts are, for example, aliphatic amines such as methylamine, ethylamine, propylamine, butylamine, pentylamine, hexylamine, heptylamine, octylamine, isopropylamine, triallylamine; aromatic amines such as aniline, benzylamine, pyridine; hexamethylenetetramine, triethylamine, diisopropylethylamine, diazabicylo[2,2,2]octane, N,N-dimethylbenzylamine, N-methyldiphenylamine, N-ethyl-3,3'-diphenyl-dipropylamine, N-alkylmorpholine, such as N-methylmorpholine, or else triton B. These amines being possibly combined with an organic or mineral acid; said acid is preferably selected from formic acid, acetic acid, propanoic acid and butanoic acid, phosphoric acid and sulfuric acid.

The addition of the methyl mercaptan is advantageously acid-base catalyzed, for example by means of a catalyst consisting of a combination of an organic or mineral acid and an organic or mineral base. Acetic acid is preferably used.

On the industrial scale, the liquid or gaseous methyl mercaptan is channeled into a reactor containing the aqueous solution, previously concentrated or unconcentrated, degassed or not degassed, KMB, or methionol, or methional.

The condensation between CAV, CALV, CADV and methyl mercaptan may be conducted in batch or continuously. They are simultaneously or alternatively introduced, by respecting the stoichiometric ratio. However, it is possible to consider working in default or excess of methyl mercaptan, depending on the continued reaction.

The reaction may be carried out by continuous introduction between the aqueous solution of the compound (I) and the gaseous methyl mercaptan in a gas/liquid reactor. In this case, the methyl mercaptan might be co- or counter-flow added. Alternatively, the reaction may be carried out by continuous introduction of the aqueous solution of the one or more unsaturated derivative(s) and liquid methyl mercaptan into a batch or piston reactor. The reaction temperature should not exceed 80° C.

The condensation catalysts between the unsaturated derivatives and methyl mercaptan are generally selected depending on several criteria:
- the conversion and the yield to 2-oxo-but-3-enoic acid (CAV) or hydroxybut-3-en-2-one (CALV) or 2-oxo-but-3-en-1-al (CADV)
- the reaction kinetics;
- the selectivity and tendency to co-produce undesirable impurities, which are, usually, high molecular weight species, resulting from parasitic polymerizations during the synthesis but also during the storage of the desired product;
- the ability to stabilize the product during its long storage.

The equipment in which the process according to the invention is implemented is not specific to said process.

The following examples and the figures to which they refer illustrate the synthesis of catalysts and their implementation in an oxidation process according to the invention.

EXAMPLES

Example 1: Preparation of Oxidation Catalysts for Implementing a Process According to the Invention In the preparations hereinafter, the active phase content is expressed by weight of the one or more metals consisting it relative to the weight of the support in the oxide form.

Preparation of 2% Pd/HAP (Catalyst 4)

To 4 mL of an aqueous solution of $H_2PdCl_4$ containing 20 mg of Pd was added at ambient temperature under vigorous stirring 0.98 g of hydroxyapatite (HAP, $Ca_{10}(PO_4)_6(OH)_2$), as described in the literature [K. Mori, T. Hara, T. Mizugaki, K. Ebitani, K. Kaneda, *J. Am. Chem. Soc.* (2004) 126 (34):10657-10666]).

Preparation of 2% PdPt/HAP 50-50 (Catalyst 5)

The procedure for the preparation of the catalyst 4 was used but starting with 4 mL of an aqueous solution of $H_2PdCl_4$ and $H_2PtCl_6$ containing 10 mg of Pd and 10 mg of Pt.

Preparation of 4% Pd 1% Pt/HAP (Catalyst 8)

To 10 mL of an aqueous solution of $H_2PtCl_6$ and $H_2PdCl_4$ containing 10 mg of Pt and 40 mg of Pd was added at ambient temperature 0.95 g of HAP. The solution was stirred at 40° C. for 2 h then evaporated to dryness. The resulting solid was crushed and calcined at 400° C. for 3 h.

Preparation of 5% Pd/HAP (Catalyst 9)

The procedure for the preparation of the catalyst 4 was used but starting from 10 mL of an aqueous solution of $H_2PdCl_4$ containing 50 mg of Pd and by using 0.95 g of HAP.

Preparation of 2% Pd/HAP (Catalyst 10)

The procedure for the preparation of the catalyst 8 was used but starting from 20 mL of an aqueous solution of $H_2PdCl_4$ containing 100 mg of Pd and by using 4.90 g of HAP.

Preparation of 4% Pd 1% Pt/HT (Catalyst 11)

The procedure for the preparation of the catalyst 8 was used but by using 0.95 g of Mg—Al hydrotalcite (HT, Mg/Al=5) prepared according to a procedure of the literature [N. K. Gupta, S. Nishimura, A. Takagaki, K. Ebitani, *Green Chem.* (2011) 13:824-827].

Preparation of 2% Pd/HAP without Calcination (Catalyst 12)

The procedure for the preparation of the catalyst 8 was used but after evaporation, instead of being calcined, the catalyst was dried in an oven at 70° C. for 3 days.

Example 2: Oxidation of but-3-Ene-1,2-Diol (BDO) with the Catalysts of the Example 1, According to the Invention Oxidation of BDO with the Catalyst 4

The catalyst 4 (30 mg) has been introduced into a glass tube, placed under oxygen via 3 vacuum/oxygen cycles then a BDO solution (0.1 M, 3 mL) in water has been introduced. The mixture was stirred (600 rotations/minute) at 50° C. under $O_2$ (1 atm) during 5 h. After returning to ambient temperature, the catalyst was separated by filtration and the solution was analyzed by HPLC (IR and UV detectors) and GC/GC-MS in order to determine the conversion and the selectivity of the products.

The conversion of BDO is of 73%. The selectivity for CALV is of 87%.

Oxidation of BDO with the Catalyst 5

The test procedure of the catalyst 4 was repeated but by using the catalyst 5 (30 mg).

The conversion of BDO is 55%. The selectivity for CALV is of 89%.

Oxidation of BDO with the Catalyst 5 (1 M BDO Solution)

The test procedure of the catalyst 1 was repeated but by using the catalyst 5 and a 0.1 M BDO solution (3 mL).

The conversion of BDO is of 28%. The selectivity for CALV is of 59%.

Oxidation of BDO with the Catalyst 8

The test procedure of the catalyst 4 was repeated but by using the catalyst 8 (30 mg).

The conversion of BDO is of 92%. The selectivity for CALV is of 85%.

Oxidation of BDO with the Catalyst 9

The test procedure of the catalyst 4 was repeated but by using the catalyst 9 (30 mg).

The conversion of BDO is of 88%. The selectivity for CALV is of 88%.

Oxidation of BDO with the Catalyst 10

The test procedure of the catalyst 4 was repeated but by using the catalyst 10 (30 mg).

The conversion of BDO is of 66%. The selectivity for CALV is of 87%.

Oxidation of BDO with the Catalyst 11

The test procedure of the catalyst 4 was repeated but by using the catalyst 11 (30 mg).

The conversion of BDO is of 83%. The selectivity for CALV.

Oxidation of BDO with the Catalyst 12

The test procedure of the catalyst 4 was repeated but by using the catalyst 12 (30 mg).

The conversion of BDO is of 83%. The selectivity for CALV is of 88%.

Example 3: Oxidation of but-3-Ene-1,2-Diol (BDO) with Recycled Catalysts of Example 1, According to the Invention Oxidation of BDO with the Catalyst 4 (2% Pd/HAP)

It is carried out under the conditions described in the example 3, with the catalyst 4. At the end of the reaction, the catalyst is separated from the reaction medium by centrifugation, washed 5 times with demineralized water and dried overnight at 70° C.

The BDO conversion and the selectivity of the process for CALV are illustrated in FIG. 1, for each test, the first column representing the percent conversion of BDO, the second representing the selectivity for CALV.

Oxidation of BDO with the Catalyst 5 (2% PdPt/HAP)

It is carried out under the conditions described in the example 3, with the catalyst 5. At the end of the reaction, the catalyst is separated from the reaction medium by centrifugation, washed 5 times with demineralized water and dried overnight at 70° C.

Figure 2:
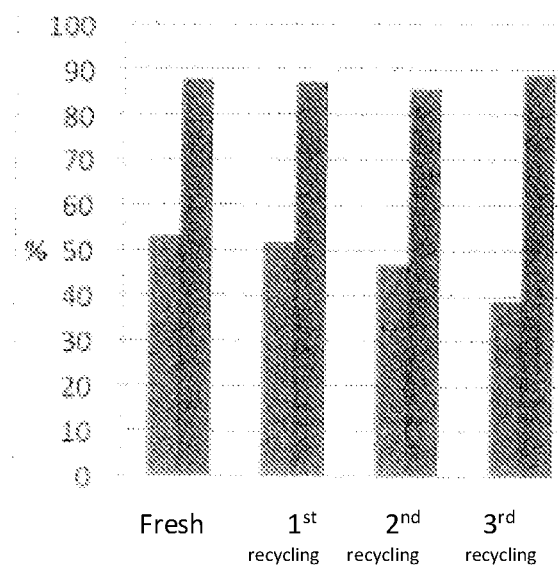
FIG. 2 shows BDO conversion and selectivity for CALV of Example 3 with catalyst.

The BDO conversion and the selectivity of the process for CALV are shown in FIG. 2, for each test, the first column representing the percent conversion of BDO, the second representing the selectivity for CALV.

It appears from this example that the catalysts of the invention are recyclable. Their recycling does not in any way affect the selectivity of the oxidation reaction and reduces only slightly the BDO conversion rate.

The invention claimed is:

1. A synthesis process of at least one compound of the following formula (III) or one of the salts thereof,

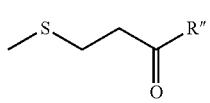
Formula (III)

wherein R" represents a CH$_2$OH, CH$_2$OR2 or CHO group for which represents an alkyl group, linear or branched, having 1 to 12 carbon atoms, and cycloalkyl groups having 3 to 12 carbon atoms, wherein but-3-ene-1,2-diol (BDO) is subjected to an oxidation in the presence of a catalyst in order to obtain at least one compound of the following formula (I) or one of the salts thereof,

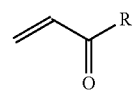
Formula (I)

wherein R represents a CH$_2$OH or CHO group, and wherein the but-3-ene-1,2-diol (BDO) is subjected to an oxidation in the presence of a catalyst, said catalyst comprising an active phase based on at least one noble metal selected from palladium, gold, silver, platinum, rhodium, osmium, ruthenium and iridium, and a support containing alkaline sites, the support comprising compounds corresponding to the following formulas A, B and C, and mixtures thereof:

$$M_\alpha[Al_{(1-b)}La_b]A^{z-}]_c \quad \text{Formula (A),}$$

wherein

M is selected from the group composed of Mg$^{2+}$, Ca$^{2+}$, Sr$^{2+}$, Ba$^{2+}$, Ra$^{2+}$, and combinations thereof, A$^{z-}$ is a monovalent or divalent anion selected from the group composed of carbonate (CO$_3^{2-}$, wherein the charge «z» is given by z=2), oxide (O$^{2-}$, wherein z=2), hydroxide (OH$^-$, wherein z=1), and bicarbonate (HCO$_3^-$, wherein z=1) or a mixture (A$^{z'-}_x$A$^{z''-}_y$) of divalent and monovalent anions with A$^{z'-}$ and A$^{z''-}$ of different anions, with A$^{z-}$ is A$^{z'-}_x$A$^{z''-}_y$ with a charge z given by z=x(z')+y(z'') and x+y=1

α varies from 0.01 to 0.4
b varies from 0.0011 to 0.11

$$c=(2\alpha/z)+[3(1-b)/z]+(3b/z)$$

$$(M_dM'_eM''_fM'''_g)_5(PO_4)_3(OH) \quad \text{Formula (B)}$$

wherein

M is Mg$^{2+}$; M' is Ca$^{2+}$; M" is Sr$^{2+}$; M'" is Ba$^{2+}$
d varies from 0 to 1
e varies from 0 to 0.5
f varies from 0 to 1
g varies from 0 to 1

$$d+e+f+g=1$$

$$(M_dM'_eM''_fM'''_g)_3(PO_4)_2 \quad \text{Formula (C)}$$

wherein

M is Mg$^{2+}$; M' is Ca$^{2+}$; M" is Sr$^{2+}$; M'" is Ba$^{2+}$
d varies from 0 to 1
e varies from 0 to 1
f varies from 0 to 1
g varies from 0 to 1

$$d+e+f+g=1,$$

if R" represents a CH$_2$OR2 group, etherification of the compound of formula (I) is carried out in order to obtain a compound of the following formula (II) or one of the salts thereof,

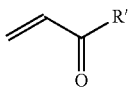

Formula (II)

wherein R' represents a CH$_2$OR2 group for which R2 represents a group selected from alkyl groups, linear or branched, having from 1 to 12 carbon atoms, and cycloalkyl groups having from 3 to 12 carbon atoms, and, said compound of formula (I) or said compound of formula (II) or said one of the salts thereof is reacted with methyl mercaptan in order to obtain said compound of formula (III) or one of the salts thereof.

2. The process according to claim 1, wherein the active phase consists of palladium or of a mixture of palladium and at least one noble metal selected from platinum and gold.

3. The process according to claim 1, wherein the active phase consists of a noble metal or a mixture of noble metals in a content ranging from 0.005 to 50% by weight relative to the weight of the support in the oxide form.

4. The process according to claim 1, wherein the catalyst comprises a promoter selected from bismuth, lead, antimony, tin, niobium, tellurium, indium, gallium, zinc, copper, nickel, cobalt, silver, tungsten, molybdenum, zirconium, vanadium, chromium, manganese, iron, cerium, praseodymium, samarium, titanium and mixtures thereof.

5. The process according to claim 1, wherein the content of the promoter of the catalyst ranges from 0.005% to 500% by weight relative to the weight of the support in the oxide form.

6. The process according to claim 1, wherein the BDO is in aqueous solution, in a concentration ranging from 1 to 70% by weight relative to the weight of the solution.

7. The process according to claim 1, wherein oxidation is carried out in the presence of a catalyst whose active phase is selected from palladium and the mixtures of palladium and platinum and the compound of formula (I) is vinyl keto alcohol (CALV).

8. The process according to claim 7, wherein compound of formula (III) is 1-hydroxy-4-methylthiobutan-2-one.

9. A synthesis process of at least one compound of the following formula (III) or one of the salts thereof,

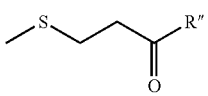

Formula (III)

wherein R" represents a CH$_2$OH, CH$_2$OR2 or CHO group for which R2 represents an alkyl group, linear or branched, having 1 to 12 carbon atoms, and cycloalkyl groups having 3 to 12 carbon atoms, wherein but-3-ene-1,2-diol (BDO) is subjected to an oxidation in the presence of a catalyst in order to obtain at least one compound of the following formula (I) or one of the salts thereof,

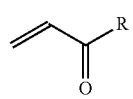

Formula (I)

wherein R represents a CH$_2$OH or CHO group, and wherein the but-3-ene-1,2-diol (BDO) is subjected to an oxidation in the presence of a catalyst, said catalyst comprising an active phase based on at least one noble metal selected from palladium, gold, silver, platinum, rhodium, osmium, ruthenium and iridium, and a support comprising at least one of hydrotalcites (HT), brucites, hydroxyapatite Ca$_{10}$(PO$_4$)$_6$(OH)$_2$, tricalcium phosphate Ca$_3$(PO$_4$)$_2$, calcium hydrogenphosphate CaHPO$_4$ (0-2)H$_2$O, calcium diphosphate Ca$_2$P$_2$O$_7$, octacalcium phosphate Ca$_8$H$_2$(PO$_4$)$_6$.5H$_2$O, tetracalcium phosphate Ca$_4$(PO$_4$)$_2$O, and amorphous calcium phosphates Ca$_3$(PO$_4$)$_2$.nH$_2$O, the support containing alkaline sites, if R" represents a CH$_2$OR2 group, etherification of the compound of formula (I) is carried out in order to obtain a compound of the following formula (II) or one of the salts thereof,

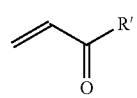

Formula (II)

wherein R' represents a CH$_2$OR2 group for which R2 represents a group selected from alkyl groups, linear or branched, having from 1 to 12 carbon atoms, and cycloalkyl groups having from 3 to 12 carbon atoms, and, said compound of formula (I) or said compound of formula (II) or said one of the salts thereof is reacted with methyl mercaptan in order to obtain said compound of formula (III) or one of the salts thereof.

10. The process according to claim 9, wherein the active phase consists of palladium or of a mixture of palladium and at least one noble metal selected from platinum and gold.

11. The process according to claim 9, wherein the active phase consists of a noble metal or a mixture of noble metals in a content ranging from 0.005 to 50% by weight relative to the weight of the support in the oxide form.

12. The process according to claim 9, wherein the catalyst comprises a promoter selected from bismuth, lead, antimony, tin, niobium, tellurium, indium, gallium, zinc, copper, nickel, cobalt, silver, tungsten, molybdenum, zirconium, vanadium, chromium, manganese, iron, cerium, praseodymium, samarium, titanium and mixtures thereof.

13. The process according to claim 9, wherein the content of the promoter of the catalyst ranges from 0.005% to 500% by weight relative to the weight of the support in the oxide form.

14. The process according to claim 9, wherein the BDO is in aqueous solution, in a concentration ranging from 1 to 70% by weight relative to the weight of the solution.

15. The process according to claim 9, wherein oxidation is carried out in the presence of a catalyst whose active phase is selected from palladium and the mixtures of palladium and platinum, the alkaline site support is selected from hydroxyapatite and hydrotalcite, and the compound of formula (I) is vinyl keto alcohol (CALV).

16. The process according to claim 15, wherein compound of formula (III) is 1-hydroxy-4-methylthiobutan-2-one.

17. The process according to claim 9, wherein said support is modified in order to make it more alkaline.

* * * * *